United States Patent [19]

Holder

[11] Patent Number: 4,798,720

[45] Date of Patent: Jan. 17, 1989

[54] NAIL POLISH DRYING COMPOSITION

[76] Inventor: William L. Holder, 341 Doverglen Dr., Antioch, Tenn. 37013

[21] Appl. No.: 932,089

[22] Filed: Nov. 18, 1986

[51] Int. Cl.[4] .......... A61K 7/043

[52] U.S. Cl. .......... 424/61; 106/3

[58] Field of Search .......... 424/61, 81; 132/73; 106/3, 4, 310

[56] References Cited

U.S. PATENT DOCUMENTS

| | | | |
|---|---|---|---|
| 1,878,103 | 9/1932 | Bradley | 424/61 |
| 2,195,971 | 3/1940 | Peter et al. | 167/85 |
| 3,749,769 | 7/1973 | Sugiyama et al. | 424/61 |
| 3,928,113 | 12/1975 | Rosenberg | 156/344 |
| 4,104,333 | 8/1978 | Lee, Jr. et al. | 260/885 |
| 4,126,144 | 11/1978 | Duarte | 132/73 |
| 4,126,675 | 11/1978 | Boulogne et al. | 424/61 |
| 4,158,053 | 6/1979 | Greene et al. | 424/61 |
| 4,229,431 | 10/1980 | Lee, Jr. et al. | 424/61 |
| 4,260,701 | 4/1981 | Lee, Jr. | 424/61 X |
| 4,289,752 | 9/1981 | Mahieu et al. | 424/47 |
| 4,381,294 | 4/1983 | Bouillon et al. | 424/61 |
| 4,384,058 | 5/1983 | Galante | 424/61 X |
| 4,409,203 | 11/1983 | Gordon et al. | 424/61 |
| 4,495,172 | 1/1985 | Orlowski et al. | 424/61 |
| 4,601,901 | 7/1986 | Guillon et al. | 424/61 |

*Primary Examiner*—Ellis P. Robinson
*Assistant Examiner*—Susan S. Rucker
*Attorney, Agent, or Firm*—Robert C. Kain, Jr.

[57] ABSTRACT

A novel composition useful for treating nails is disclosed. The composition is prepared by mixing commercially available top coat nail polish, acrylic nail powder, acrylic nail primer and an adhesive in desired amounts. The resultant composition reduces the drying time of nail polish from three to five minutes and provides a superior gloss. The product can be used on either natural or acrylic nails.

2 Claims, No Drawings 

NAIL POLISH DRYING COMPOSITION

BACKGROUND OF THE INVENTION

1. Field of the Invention

This invention relates to a composition to be used when treating fingernails and toenails, more specifically, to a composition used to decrease the drying time during manicures or pedicures and used to give the nail improved gloss.

2. Description of Prior Art

Traditionally, when one performs a manicure or pedicure, after sufficiently cleaning and drying the nails, a layer of base coat nail polish is applied to the surface of the nail. The base coat polish is typically colorless. Thereafter, coats of colored nail polish are sequentially applied to the nails. Typically, up to three coats of colored polish are applied, and more typically, two coats are applied. Thereafter, a layer of top coat colorless nail polish is applied onto the colored nail polish. This sequence of base coat, colored polish, and top coat polish remains substantially the same, whether the nails are natural or acrylic.

The above mentioned manicure or pedicure process suffers from a number of defects. First, three different compositions need to be used, a base coat polish, a colored polish, and a top coat polish.

Additionally, although the base coat/colored polish/top coat polish procedure is typically used, a long period of time is required for the colored polish to completely dry; typically from at least 15 to 30 minutes, and possibly longer.

Therefore, when an individual is in a hurry, such as a professional business woman, it is impossible to have an adequate amount of time for a manicure or pedicure. This can be particularly detrimental when the business woman is meeting a client or making a presentation and wants her nails to have a manicured look.

In addition, after nails have been manicured, they begin to lose the freshly polished look after a short period of time; typically from a few days to two weeks. Therefore, if one wishes to keep their nails in a "freshly manicured" condition, they can only do so by having frequent manicures.

Therefore, there exists a need for a composition which is to be used in connection with colored nail polish to reduce the drying time of the colored polish. Further, there exists a need for reducing the number of chemicals used by cosmetologists when performing manicures. Further, there exists a need for a composition which can give nails a freshly polished appearance for extended periods of time.

SUMMARY OF THE INVENTION

Thus, a purpose of the present invention is to provide a composition to be used in connection with colored nail polish which performs the benefits of reducing the drying time of the colored nail polish and in addition gives the nails a freshly polished look for extended periods of time. The inventor has discovered that by mixing commercially available products in specified amounts, such a composition can be obtained. Specifically, by combining acrylic nail powder, acrylic nail primer, an adhesive, and top coat nail polish in specified amounts, a composition is produced which significantly reduces the drying time normally needed for colored nail polish. To use the composition, it is recommended that the composition be applied as a base coat layer, that a colored polish be coated on top of the composition, that the composition then be recoated on top of the polish, then another coat of colored polish be applied over the composition, and finally, the composition be applied over the colored polish. By using the composition of the invention, and the five step coating sequence described above, drying times for the colored polish are significantly reduced, the nails maintain a freshly polished look for extended periods of time, and the necessity for having different base coat and top coat polishes are eliminated.

Thus, it is an object of the present invention to provide a composition to be used in connection with colored nail polish wherein the drying time of the colored polish is significantly reduced by applying the composition as a base, intermediate and top coat coating.

A further object of the present invention is to provide a composition which eliminates the need for having a separate base coat polish and top coat polish.

It is a further object of the present invention is to provide a composition which gives nails a freshly polished look for extended periods of time.

A further object of the present invention is to provide a composition which can be applied onto the nails after a manicure or pedicure has been performed to enable the nails to maintain a freshly polished look.

It is a further object of the present invention to provide a composition which may be successfully used with both natural and acrylic nails.

Other objects and features of the present invention will become apparent to those skilled in the art as the disclosure is made in the following description of the preferred embodiment of the present invention.

DETAILED DESCRIPTION OF THE PREFERRED EMBODIMENT

In describing the invention, specific terminology will be resorted to for the sake of clarity. However, the invention is not intended to be limited to the specific terms so selected, and it is to be understood that each specific term selected includes all technical equivalents which operate in a similar manner to accomplish a similar purpose.

The composition of the present invention is prepared by mixing several commercially available products. Specifically, the commercially available products used are a top coat polish, an acrylic nail powder, an acrylic nail primer, and an adhesive. The resultant composition will contain solid material dispersed in a solvent.

Specifically, the top coat polish should contain the following chemicals: butyl acetate, toluene nitrocellulose, ethyl acetate, isopropyl alcohol, dibutyl phthalate and camphor. Such a top coat polish is commercially available from United Nails of Orange, Tex. Additionally, the top coat may include, but not be limited to isostearic hydrolyzed animal protein, acrylic copolymers, toluene sulfonamide/formaldehyde resin, benzophenone-1, polyester resin, titanium dioxide, iron oxides, D & C Red #6, barium lake, D & C Yellow #5, zirconium lake, D & C Violet #2, ferric ammonium ferrocyanide, octrizole. Such top coat polishes typically are packaged in one-half ounce bottles.

The nail powder to be used should be made primarily of acrylic ester polymers. Additionally, the powder may contain benzoyl peroxide, titanium dioxide, silica, and FD & C Red #17. One such nail powder which can be used to prepare the claimed composition is ALPHA 9 Fine Grind Powder which is manufactured by J.D.S. Manufacturing Company of Van Nuys, Calif. It is envisioned that other acrylic powders besides ALPHA 9 may be practiced within the scope of the invention.

The primer to be used to prepare the composition should contain acrylic ester monomers. Additionally, the primer may contain dimethyl p-toluidine, BHT and other acrylics. One such primer which can be used is "Super Nail" Lift No More Primer manufactured by American International Industries of North Hollywood, Calif. It is envisioned that other acrylic primers may be practiced within the scope of the invention.

The adhesive to be used is preferably a cyano-acrylate resin. One such adhesive which can be used to make the claimed composition is Krazy Glue, manufactured by Krazy Glue Incorporated of Itasca, Ill. It is envisioned that other strong adhesives may be practiced within the scope of the invention, particularly those containing cyano-acrylate resins.

By way of illustration, but not by way of limitation, the following examples are given in accordance with the present invention.

EXAMPLE 1

24 one-half ounce bottles of a top coat nail polish obtained from United Nails of Orange, Tex. containing butyl acetate, toluene nitrocellulose, ethyl acetate, isopropyl alcohol, dibutyl phthalate, toluene sulfonamide/formaldehyde resin, camphor, isostearic hydrolyzed animal protein, acrylates copolymer and benzophenome-1 are poured into a commercial blender. Thereafter, 1.075 of ALPHA 9 Fine Grind Powder is added to the top coat polish along with ICC Supernail Lift No More Primer and ICC of Krazy Glue. The blender is then activated at high speed agitation for two to four minutes at room temperature.

The obtained composition was analyzed and found to contain the following:

| ANALYSIS OF PRODUCT | |
|---|---|
| Total Solids, % (plastic) | 24.57% |
| Volatile Matter, % (solvents) | 75.43% |
| | 100.00% |
| ANALYSIS OF SOLIDS | |
| Acrylic Resin | 20.00% |
| Cyano-acrylic Resin | 4.57% |
| | 24.57% |
| ANALYSIS OF VOLATILE MATTER | |
| Ethyl Alcohol | 48.80% |
| Acetone | 16.06% |
| Ethylene Glycol Monomethyl Ether | 27.11% |
| Ethylene Glycol Monobutyl Ether | 8.03% |
| | 100.00% |

EXAMPLE 2

The composition prepared in Example 1 was used with Wet and Wild ® polish in a manicure. The composition of Example 1 was first coated onto a human nail as a base coat. Thereafter, one coat of Wet and Wild ® polish was applied directly on top of the base composition. Thereafter, the composition prepared according to Example 1 was coated on top of the nail polish and another coat of Wet and Wild ® polish was applied on top of the composition. Finally, a top coat of the composition according to Example 1 was coated onto the nail as a top coat. Therefore a total of five coats of polish/composition was applied to the nail. By using such an arrangement, the colored nail polish dried in 3½ minutes. The nail finish exhibited a superior gloss.

EXAMPLE 3

The composition prepared according to Example 1 was used in combination with a colored polish manufactured by Maybelline ®. Three coats of the colored polish and three coats of the composition according to Example 1 were coated onto a fingernail. The drying time was approximately 3½ minutes. The nail finish exhibited a superior gloss.

EXAMPLE 4

The composition according to Example 1 was used in connection with a colored polish manufactured by L'Oreal ®. The composition according to Example 1 and the colored polish were applied alternatively until four coats of the composition and three coats of the colored polish were applied. The drying time of the colored polish was three minutes. The nail finish exhibited a superior gloss.

EXAMPLE 5

By way of comparison, the test set forth in Example 2 was repeated except that the composition as set forth in Example 1 was replaced by the colorless polish used to prepare the composition in Example 1. Drying time was from 15 to 30 minutes.

The above described composition can be successfully used on both natural and acrylic nails. Further, to retain a freshly polished look, a coating of the inventive composition should be applied to the top surface of the polished nail periodically. In the case of natural nails, the composition should be applied every 2 to 3 days. In the case of acrylic nails, the composition should be applied every 3 to 4 days.

In addition to the above-mentioned properties, the inventive composition is non-chipping and can dry up to one to seven coats of nail polish in three to five minutes.

From the above, it should be apparent that many modifications and variations of the present invention are possible. It is therefore to be understood that, within the scope of the appendent claims, the invention may be practiced otherwise than as specifically described.

What is claimed is:
1. A nail coating composition, said composition having a solid material comprising about 25% by weight of said composition and a solvent content comprising about 75% by weight of said composition, and said composition being a combination of a colorless nail polish, an acrylic nail powder, an acrylic nail primer and cyanoacrylate adhesive.
2. The composition of claim 1 wherein said solvent comprises about 50% ethyl alcohol, about 15% acetone, about 25% ethylene glycol monomethyl ether, and about 8% ethylene glycol monobutyl ether.

* * * * *